United States Patent [19]

Deutsch

[11] Patent Number: 5,002,754

[45] Date of Patent: Mar. 26, 1991

[54] TECHNETIUM (III/II) IMAGING AGENTS

[75] Inventor: Edward A. Deutsch, Cincinnati, Ohio

[73] Assignee: University of Cincinnati, Cincinnati, Ohio

[21] Appl. No.: 207,281

[22] Filed: Jun. 15, 1988

[51] Int. Cl.[5] ..................... A61K 49/02; C07F 13/00
[52] U.S. Cl. ........................................ 424/1.1; 534/14
[58] Field of Search ........................... 424/1.1; 534/14

[56] References Cited

U.S. PATENT DOCUMENTS

| | | | |
|---|---|---|---|
| 3,795,626 | 1/1989 | Deutsch et al. | 424/1.1 |
| 4,419,339 | 12/1983 | Neirinckx | 424/1.1 |
| 4,451,450 | 5/1984 | Subramanyam | 424/1.1 |
| 4,455,291 | 6/1984 | Tweedle | 424/1.1 |
| 4,489,054 | 12/1984 | Deutsch | 424/1.1 |
| 4,497,790 | 2/1985 | Rodriguez | 424/1.1 |
| 4,512,967 | 4/1985 | Linder | 424/1.1 |
| 4,789,543 | 12/1988 | Linder | 424/1.1 |

OTHER PUBLICATIONS

M. Neves et al, Reprinted from Technetium in Chemistry and Nuclear Medicine 2, 123-126.

M. Neves et al, Nucl. Med. Biol., vol. 14, No. 5, pp. 503-510, 1987.
N. de Vries et al, Inorg. Chem., 1988, 27, 1574-1580.
A. Davison et al, Inorganica Chimica Acta, 120 (1986), L15-L16.
U. Abram, Appl. Radiat. Isot., vol. 39, No. 5, pp. 385-390 (1988).

*Primary Examiner*—John S. Maples
*Attorney, Agent, or Firm*—Wood, Herron & Evans

[57] ABSTRACT

A ligated technetium (III/II) complex is useful as a brain perfusion imaging agent. The complex has a technetium (III/II) center surrounded by six ligating moieties. The complex preferably has a reduction potential Tc(III) to Tc(II) which is less than about +0.6 volts vs Ag/AgCl (3M NaCl) and at least low enough to be oxidized in vivo after crossing the blood brain diffusion barrier. The technetium complex has six ligating moieties, four of which use phosphorous, arsenic, or nitrogen as ligating atoms. The remaining two ligands use sulfur or selenium to complex to the Tc center. These ligands are modified to establish an effective oxidation potential of the Tc(II) thus providing the necessary redox potential for in vivo oxidation.

13 Claims, No Drawings

TECHNETIUM (III/II) IMAGING AGENTS

Funding for the research leading to this invention was provided in part by the National Institute of Health. Therefore, the United States Government is hereby granted a paid up non-exclusive royalty free license to practice the present invention.

Technetium-99m complexes are used for a wide range of imaging purposes. Both cationic and anionic complexes are used to image various organs of the human body. The ability of 99m-Tc complexes to produce detectable gamma radiation as well as the ready availability of this isotope makes 99m-Tc an important diagnostic tool.

The potential of single photon emission computed tomography imaging techniques and diagnosis in management of cerebral vascular disease has been studied extensively in the context of brain perfusion. Xe-133 has been used for some time to determine regional cerebral blood flow. But tomographic imaging with this isotope requires specially dedicated instrumentation which is not optimal for other tomographic applications.

Much more useful results have been obtained in the past few years with I-123 labelled amines. These amines exhibit high brain uptake, long cerebral retention time and clinical studies with these have clearly demonstrated the ultimate utility of single photon emitting radiopharmaceuticals that monitor regional cerebral blood flow. However, since I-123 must be produced in a cyclotron and possesses a physical half life of 13.3 hours, it is expensive and not universally available for daily use.

Clearly, the ideal brain perfusion imaging agent should be based on the readily available, inexpensive Tc-99m isotope. The search for a radio-pharmaceutical which would penetrate the blood-brain barrier (BBB) and have prolonged retention time in the brain has been pursued vigorously since 1978.

While Tc-99m brain perfusion imaging agents have been systematically sought since 1978, it has only been in the last three years that significant progress toward such complexes have been achieved. Neutral Tc(V) complexes containing derivatives of tetradentate $N_2S_2$ dithiol ligand $HSCH_2CH_2NHCH_2CH_2NHCH_2CH_2SH$ have been shown to cross the BBB. But the underivatized complexes are not sufficiently retained in the brain. Attachment of pendant amine functionalities to the core Tc(V) complexes leads to significant brain retention in primates similar to the brain retention observed for the I-123 labelled amines. But these do not function well in humans.

A totally different class of neutral Tc(V) complexes containing derivatives of tetradentate-$N_4$ bis(oxime) ligand has been also shown to cross the BBB and several of these complexes are retained in the brain long enough to allow clinically useful images to be obtained in humans. These compounds are inherently unstable and must be used within 30 minutes after formulation. This presents inherent problems in clinics. Further, these present certain interpretational problems.

Further, a series of neutral Tc(II) complexes and cationic Tc(III) complexes which are reduced to their neutral Tc(II) forms in vivo, have been evaluated as brain imaging agents. However, none of these complexes are sufficiently retained in the brain to provide an effective image. See "Neutral Tc(II) 99m Complexes as Potential Brain Perfusion Imaging Agents", *Nuclear Medicine Biol.*, Vol. 14, 5, pages 503–510 (1987).

Others have investigated the potential utility of redox reactions occurring after crossing the BBB. Bodor, PCT application no. PCT/US85/01334 discusses a redox reaction of ligated Tc(V) wherein the ligand contains a dihydropyridine moiety which is oxidized to a pyridinium salt. See also PCT application no. PCT/US85/01333 These references discuss the oxidation of the ligand as opposed to the metal center and of course do not suggest that the oxidation or reduction of the metal center will have any effect on the biological fate of the complex. Unfortunately, these have not been found to provide an effective imaging agent for humans.

There has been a great deal of work conducted with respect to cationic technetium blood imaging agents and from a chemical point of view, this art has been well developed. Various potential ligands and systems are disclosed in Deutsch, U.S. Pat. No. 4,489,054, Jones, U.S. Pat. No. 4,452,774, Dean, U.S. Pat. No. 4,582,700, Glavan, U.S. Pat. No. 4,374,821, Linder, U.S. Pat. No. 4,512,967. Further, Deutsch application Ser. No. 172,969, filed Mar. 11, 1986, discloses a Tc(III) complex which is non-reducible in vivo to provide an improved heart imaging agent.

Of course, none of these heart imaging agents are effective brain imaging agents. In light of this, there still remains a need for an effective brain imaging agent which provides an accessible source of technetium$^{99m}$, which crosses the blood brain diffusion barrier and remains in the brain for a period of time effective to obtain a good image of the brain. Of course, it must be one which also does not have any adverse side effects.

SUMMARY OF THE INVENTION

The present invention is premised on the realization that such an effective single photon emission computed tomographic imaging agent can be obtained using the neutral Tc(II)-99m complex. The invention is further premised on the realization that these complexes are particularly effective as brain imaging agents where the reduction potential Tc(III) to Tc(II) of the Tc(II) complex is such that upon crossing the blood brain diffusion barrier, the Tc(II) complex is oxidized to a Tc(III) complex. This oxidation state of the Tc(III) complex impedes the crossing of the blood brain diffusion barrier, thus keeping the imaging agent in the brain for an effective period of time.

The present invention is further premised on the discovery of a new class of 99m technetium complexes. These said complexes have the following general formula:

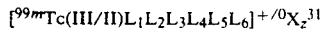

and more particularly

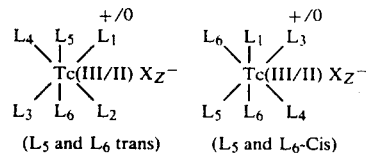

In this formula X is a pharmaceutically acceptable anion and Z is 0 or 1 depending on the oxidation state of the Tc center.

Wherein $L_1$-$L_4$ are ligands which coordinate through phosphorous, arsenic, or nitrogen and $L_5$ and $L_6$ are ligands which coordinate through sulfur or selenium atoms. The choice of $L_1$-$L_4$ and $L_5$, $L_6$ ligands controls the effective redox potential of the Tc(II)/Tc(III) redox complex and provide a reduction potential Tc(III) to Tc(II) which is low enough to permit oxidation in vivo.

X represents a parentally acceptable anion such as a halogen. If the Tc complex is in the plus two state, Z is 0 and the complex is neutral. If the Tc center is in the plus three state, Z is one and the complex is a cation. As will be demonstrated further, the complex can be easily converted from a Tc(II) complex to a Tc(III) complex and back again.

The invention will be further appreciated in light of the following detailed description.

DETAILED DESCRIPTION

The complex of the present invention is a $^{99m}$Tc(III/II) complex. The octahedrally coordinated Tc center has six coordination bonding sites, two designated trans and four designated cis. These bonding sites are occupied by six ligating moieties. A ligating moiety is a complex which has an atom which has electron density available for donation to the technetium center. The ligating moieties may be bonded together providing two atoms with electron density available to the technetium center. These could be multidentate ligands such as bidentate ligands.

The complex of the present invention can be expressed by one of the following general formulae:

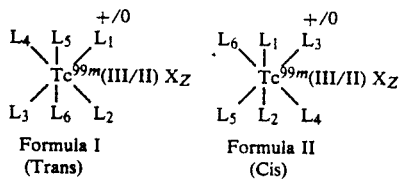

Formula I (Trans)    Formula II (Cis)

X represents a parentally acceptable anion such as a halogen. If the Tc center is in the plus two state, Z is zero and there is no anion present. If the Tc center is in the plus three state, Z is one.

According to the present invention, the ligands $L_1$-$L_4$ shall be referred to as the primary ligands. This appellation is used only as a means to distinguish these ligands from $L_5$ and $L_6$ which will be referred to as the secondary ligands. This reference, primary and secondary, however, has no scientific significance.

The primary ligands have a formula $(R_i)_3$-A: wherein A represents P, As, or N. In this formulation, i represents an integer from 1–4 corresponding to the subnumeral for the respective ligands L. $R_1$-$R_4$ independently represents the same or different radical including hydrogen, $C_1$-$C_{20}$ alkyl which is intended to include substituted and unsubstituted alkyl, oxy alkyl ($C_1$-$C_{10}$) (i.e., —O—$CH_3$), cycloaklyl ($C_3$-$C_{10}$), as well as aryl which is also intended to include substituted and unsubstituted aryl such as arylene alkyl, aryl halide, and heterocyclic aromatics.

Further, two, three or four Rs may be bonded together forming a bi, tri or tetradentate ligand. Examples of ligands useful in the present invention are disclosed in a series of different applications including Linder, U.S. Pat. No. 4,512,967, Glavan, U.S. Pat. No. 4,374,821, Dean, U.S. Pat. No. 4,582,700, Deutsch, U.S. Pat. No. 4,387,087.

The ligands which are conventionally used in technetium heart imaging are generally useful as primary ligands. These ligands include:

DMPE(($CH_3)_2$P—$CH_2CH_2$—P($CH_3)_2$)
diars (O—$C_6H_4$(As($CH_3)_2)_2$
diphos (($C_6H_5)_2$—$CH_2CH_2$—P($C_6H_5)_2$)
tris (1-pyrazolyl)borato
porphyrin
cyclam, 1,4,8,11-tetraazacylotetra decane and derivatives
tetraphos P($CH_2CH_2$P($C_6H_5)_2)_3$
DAE (($C_6H_5)_2$As—$CH_2CH_2$NH$CH_2CH_2$NH$_2$)
DIEN($H_2$N—$CH_2CH_2$NH$CH_2CH_2$NH$_2$)
TRIEN $H_2$N$CH_2CH_2$NH$CH_2CH_2$NH$CH_2CH_2$NH$_2$
1,2-bis(ditoluylphosphino)ethane
1,2-bis(di(trifluoromethyl)phosphino)ethane
1,2-bis(dimethylphosphino)-1,1-difluoroethane
1,2-bis(dimethylphosphino)-1-fluoroethane
1,2-bis(dimethylphosphino)propane
1,2-bis(di(trifluoromethyl)phosphino)-1,1,2,2-tetrafluoroethane
1,2-bis(di(trifluoromethyl)phosphino)propane
2,3-bis(di(trifluoromethyl)phosphino)butane
1,2-bis(di(trifluoromethyl)phosphino)butane
1,3-bis(dimethylphosphino)butane
1,3-bis(dimethylphosphino)propane
1,3-bis(di(trifluoromethyl)phosphino)propane
1,2-bis(dimethylphosphino)-1,1-dichloro-2,2-difluoroethane
1,2-bis(diethylphosphino)ethane
1,2-bis(diisopropylphosphino)ethane
1,2-bis(dipropylphosphino)ethane
1-dimethylphosphino-2-diisopropylphosphinoethane 1,2-bis(diisobutylphosphino)ethane
1-dimethylphosphino-2-dimethylarsinoethane.

The secondary ligands have the formula $R_n$—Y$^-$: wherein Y represents sulfur or selenium and $R_n$ represents H or an organic radical. The numeral n represents 5 or 6 to indicate correspondence to ligand $L_5$ or $L_6$ These monodentate ligands have a charge of minus one. More specifically, $R_5$ and $R_6$ can represent the same or different radical including $C_1$-$C_{20}$ alkyl (substituted and unsubstituted), aryl (substituted and unsubstituted), alkylene aryl, substituted carbonyl such as amides, carbamates as well as alkyl substituted carbonyls. Radicals which accept electron density such as halides are particularly suitable substitutes for both alkyl and aryl compounds. Further the R can represent a sulfanyl containing radical and thus represent a xanthyl or sulfonamide. Specific groups represented by R include:

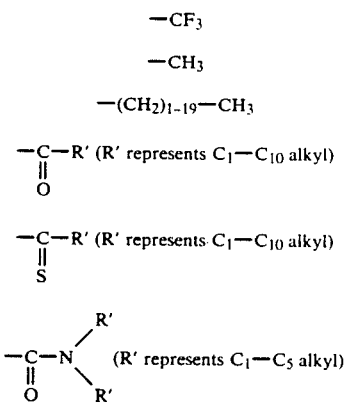

-continued

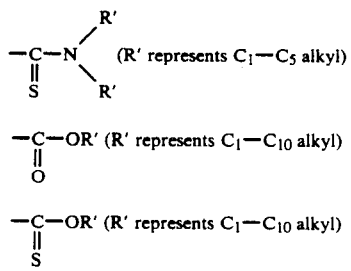

—C—OR' (R' represents $C_1$—$C_{10}$ alkyl)
 ‖
 O

—C—OR' (R' represents $C_1$—$C_{10}$ alkyl)
 ‖
 S

Making the radical bonded to the sulfur or selenium either more or less electro negative makes the complex itself more easily or more difficultly oxidized.

A complex is designated cis where the two secondary ligands are adjacent each other (Formula II). A trans complex indicates the secondary ligands are opposite each other (Formula I).

The single photon emission computed tomographic imaging agent of the present invention is a Tc(III/II) complex which preferably has a reduction potential Tc(III)-Tc(II) of less than about +0.6 volts vs. Ag-/AgCl (3M NaCl) and also low enough to provide for oxidation of the Tc(II) complex upon crossing the blood brain diffusion barrier. Further, this complex, since it is injected into the blood, must be stable enough in the Tc(II) state to avoid oxidation in the blood stream during the few seconds (at least about 2 seconds) required for transport to the brain. For this reason, the reduction potential Tc(III) to Tc(II) should generally be from about +0.6 to about −0.4 volts, and optionally from about +0.4 to about +0.2 volts as measured versus a Ag/AgCl (3 M NaCl) reference electrode by electrochemical techniques that are well known in the art.

The groups $R_5$ and $R_6$ attached to the sulfur or selenium have a substantial influence on the reduction potential of the $^{99m}$Tc center. Basically, making these radicals more electron donating increases the reduction potential of Tc(III) to Tc(II). An R group which is electron withdrawing (for example, a halogenated methyl group —$CF_3$) has the opposite effect.

The radicals $R_1$–$R_4$ have a similar although less pronounced effect.

These Tc(III/II) complexes can be made in a two step process. These complexes are prepared from pertechnetate-99m which is obtained from a 99-molybdenum generator. This can be further purified according to the method disclosed in Deutsch et al, U.S. Ser. No. 802,779 filed Nov. 27, 1985 which uses a lipophillic counter ion bound to the pertechnetate-99m which is then separated from impurities by preferential sorption such as elution from a Sephadex column.

The obtained 99m-pertechnetate can be complexed with the primary ligands to form a Tc(V) complex having the following general formula:

[$^{99m}$Tc(V)O(OH)$L_1$–$L_4$]$^{+2}$

The Tc(V) complex is then reduced to the Tc(III/II) complex by reducing the technetium(V) complex in the presence of the secondary ligand.

Alternately the pertechnetate is reacted with the secondary ligand first to form a Tc(III) complex. This is then reacted with the primary ligand to form a mixed ligand Tc(III) complex. Where the primary ligand is a tetradentate ligand it takes up four of the six available bonding sites leaving two which must be filled with the monodentate secondary ligand. Because the primary ligands bond more strongly to the Tc center, this method is most useful when the primary ligands are tetradentate.

FIRST GENERAL EXAMPLE

The 99m-pertechnetate solution is obtained from a 99-Mo generator. This method of obtaining 99m-Tc is well known to those skilled in the art and is disclosed for example in Deutsch et al U.S. Pat. No. 4,489,054 incorporated herein by reference and Glavan et al U.S. Pat. No. 4,374,821 also incorporated herein by reference. The 99m-pertechnetate is eluted from the 99-Mo generator and is diluted to the desired concentration of 99m-Tc activity of 10–100mCi/mL with normal saline.

Pertechnetate-99m is extracted from saline (generator eluent) as $(C_4H_9)_4N^{99m}TcO_4$ using a reversed phase ($C_{18}$) cartridge (Waters). The method involves the addition of an excess $(C_4H_9)_4NBr$ (0.01 M) to the saline solution containing $Na^{99m}TCO_4$. The mixture is passed through the reversed phase cartridge and the retained $(C_4H_9)_4N^{99m}TcO_4$ is washed thoroughly with water to remove the interfering ions and then eluted with 0.5 to 1 mL of ethanol.

0.5 mL of an ethanolic solution containing the desired amount of activity (mCi's) is transferred to a 5 mL borosilicate vial. The solution is acidified with 10 microliters of 1 M trifluoromethyl sulfonic acid (triflic acid, $CF_3SO_3H$). The solution is degassed with argon for about 3 minutes and while degassing, 50 microliters of neat thiol (RSH) are added (RSH represents separately for example benzyl mercaptan, p-methoxybenzyl mercaptan, 1-mercaptopropane, ethyl mercaptan, methyl thioglycolate, ethyl thioglycolate or 2-mercaptoethanol.

The mixture is degassed with argon for about 30 seconds then is treated with 50 microliters of 1% primary ligand solution (in this general example Diars) in absolute ethanol. (The primary ligand solution was prepared in a dry box under argon by diluting 30 microliters of neat ligand to a volume of 3.0 mL with well degassed absolute ethanol.) The borosilicate vial is quickly capped and treated in an oil bath at 80° C. for about 5 minutes.

Preparation of 99mTc complex for use in the present invention is also disclosed in the following particular examples.

EXAMPLE 1

$^{99m}$Tc(Diars)$_2$(thioglucose-H)$_2$+ Complex

The complex Tc(Diars)$_2$(thioglucose-H)$_2$+ where thioglucose-H is a deprotonated thioglucose is prepared in the same manner described immediately above except that the synthesis requires 5 mg of solid basic sodium β-D-thioglucose (Sigma) and 40 microliter of 1 M $CF_3SO_3H$. The borosilicate vial containing the mixture of pH=2 is heated at 85° C. for 5 minutes.

EXAMPLE 2

$^{99m}$Tc(Diars)$_2$(thiocholesterol-H)$_2$+

The complex is also prepared in the same manner but in the presence of about 20 mg of thiocholesterol-H. The mixture is heated at 90–100° C. for 20 minutes. (Thiocholesterol-H represents deprotonated thiocholesterol.)

Example 3

$^{99m}Tc(Diars)_2(SCH_3)_2^+$

An ethanolic solution (0.5 mL) containing the desired activity of $(C_4H_9)_4N^{99m}TcO_4$ is acidified with 10 microliters of concentrated $CF_3SO_3H$. The solution is degassed (argon) in a 5 mL borosilicate vial for about 5 minutes. While degassing, 80 microliters of 1% Diars solution in absolute ethanol are added followed by a quick addition of 3 mg of sodium thiomethoxide (in a hood). The vial is quickly capped. The generated $CH_3SH$ which is essential for the synthesis of the complex is a gas at room temperature (B.p. =6° C.). The vial is heated at 85° C. for 10 minutes.

For use as brain imaging agents, the complexes made according to these examples are reduced prior to injection by making the pH of the solution alkaline and allowing the excess thiol ligand to reduce the complex to Tc(II). Alternately, reductants such as sodium borohydride can be added.

Second General Example

Cationic $^{99m}Tc(Diars)_2(SR)_2^+$ can also be formed from the reaction of $tr$-$^{99m}Tc(Diars)_2O_2^+$ and thiols (RSH) where RSH=benzyl mercaptan, $C_6H_5CH_2SH$ or p-methoxybenzyl mercaptan, $CH_3O-C_6H_4-CH_2SH$.

Ethanolic solutions (pH=2-3) of $tr$-$Tc(Diars)_2O_2^+$ are treated with 20-50 microliters of neat thiols then degassed for 3 minutes. The borosilicate vial containing the above mixture is heated at 80° C. for 10 minutes; then allowed to cool to room temperature. This method can be applied for the preparation of other cationic $Tc(Diars)_2(SR)_2^+$ as an alternative method.

EXAMPLE 4

Synthesis of $[tr$-$^{99m}Tc(Diars)_2O_2]+$ in ethanol and in the absence of the chloride ion The 0.5 mL of $(C_4H_9)_4N^{99m}TcO_4$ in ethanol is transferred to a 5 mL borosilicate vial. The solution is acidified with 10 microliters of 1 M $CF_3SO_3H$ then degassed for 3 minutes. While degassing, 50 microliters of 1% Diars solution in absolute ethanol is added. The capped vial is heated at 85° C. for 5 minutes then allowed to cool to room temperature. This complex is next reduced to Tc(III) complex by adding the thiol ligand in the presence of a reducing agent as is discussed below.

The preparation of $^{99}Tc(V)$ and 99-Tc(III/II) complexes is shown by the following examples. These experiments are designed to provide information relevant to the 99mTc counterparts.

EXAMPLE 5 trans-Oxohydroxobis(1,2-bis(dimethylphosphino)ethane)technetium(V) Hexafluorophosphate, trans-[Tc(OH)O(DMPE)_2](PF_6)_2.

To a solution containing 100 mg of $NH_4TcO_4$ ($5.5 \times 10^{-4}$ mol) in 4 mL of degassed 0.05 M NaOH was added 420 mg of neat DMPE ($2.8 \times 10^{-3}$ mol), followed by 4 mL of degassed 95% ethanol. After stirring at room temperature for 15 min, 0.4 mL of concentrated $CF_3SO_3H$ was added to the yellow-orange solution. The reaction solution was stirred at room temperature for another 15 min and became deep orange-brown in color. Addition of 2 g of $NH_4PF_6$ in a small amount of water, followed by cooling in a refrigerator for 1 day, produced an orange precipitate of trans-[Tc(OH)O(DMPE)_2](PF_6)_2. Yield: 350 mg.; 88%.

EXAMPLE 6 trans-Oxohydroxobis(1,2-bis(diethylphosphino)ethane)technetium(V) Hexafluorophosphate, trans-[Tc(OH)O(DEPE)_2](PF_6)_2.

To a solution containing 100 mg of $NH_4TcO_4$ in 22 mL of degassed 0.1 M NaOH was added 800 mg of neat DEPE ($3.88 \times 10^{-3}$ mol) followed by 4 mL of degassed ethanol. After stirring at room temperature for one hour under an argon atmosphere, 0.4 mL of concentrated $CF_3SO_3H$ was added to the yellow solution. The reaction solution turned deep orange in color upon stirring 30 min longer at room temperature. When 2 g of $NH_4PF_6$ in a small amount of water was added to the deep orange solution, a white precipitate appeared. After removal of the white precipitate by filtration, the filtrate was kept in a refrigerator for 1 day. Orange crystals of trans-[Tc(OH)O(DEPE)_2](PF_6)_2 were collected by filtration. Yield: 300 mg; 65%. Anal. Calcd for trans-[Tc(OH)O(DEPE)_2(PF_6)]: C, 28.79; H, 5.92; F, 27.32; S, 22.27. Found: C, 28.58; H, 5.57; F, 27.98; S, 21.55.

To form a Tc(III/II) complex of the present invention the Tc(V) complex is reduced in the presence of a monodentate secondary ligand. This reduction is conducted in anaerobic conditions in the presence of a mild reducing agent. Generally, the ligand itself acts as a mild reducing agent. Other mild reducing agents such as sodium dithionite, $NaSCH_3$, or stannous chloride can be added.

The Tc(V) complex previously described is added to degassed ethanol with a fivefold molar excess of the secondary ligand. This mixture is heated to about 60° C. until a dramatic deep purple color change occurs.

EXAMPLE 7 trans-bis(methanethiolato)bis(1,2-bis(dimethylphosphino)ethane)technetium(III) Hexafluorophosphate, trans-[Tc(SCH_3)_2(DMPE)_2]PF_6.

To a suspension containing 100 mg of trans-[Tc(OH)(O)DMPE)_2](PF_6)_2 ($1.4 \times 10^{-4}$ mol) in 20 mL of degassed ethanol was added 100 mg of $NaSCH_3$ ($1.4 \times 10^{-3}$ mol) in 51 mL of degassed ethanol. The mixture was stirred at 60° C. for 30 min under an argon atmosphere whereupon the solution became deep purple. To this was added 0.5 mL of saturated $NH_4PF_6$ in water and the solution turned blue almost immediately. When the blue solution was cooled to room temperature a blue precipitate appeared. The blue precipitate was dissolved in a small amount of $CH_3CN$, and kept in a refrigerator for one day. The resulting crystals of trans-[Tc(SCH_3)_2(DMPE)_2]PF_6 were collected by filtration. Yield: 30 mg; 34%.

EXAMPLE 8 trans-bis(methanethiolato)bis(1,2-bis(dimethylphosphino)ethane)technetium(III) Trifluoromethylsulfonate, trans-[Tc(SCH_3)_2(DMPE)_2]CF_3SO_3.

The TFMS salt was obtained by the addition of $NaCF_3SO_3$ to an almost saturated solution of trans-[Tc(SCH_3)_2(DMPE)_2]PF_6 in acetone, followed by cooling in a refrigerator for one day. Recrystallization from acetone in a refrigerator produced crystals suitable for x-ray analysis.

EXAMPLE 9 trans-bis(methanethiolato)bis(1,2-bis(diethylphosphino)ethane)technetium(III) Hexafluorophosphate, trans-[Tc(SCH$_3$)$_2$(DEPE)$_2$](PF$_6$).

The trans-[Tc(SCH$_3$)$_2$(DEPE)$_2$]PF$_6$ complex was prepared by a method similar to that described above for trans-[Tc(SCH$_3$)$_2$(DMPE)$_2$]PF$_6$, using trans-[Tc(OH)O(DEPE)$_2$](PF$_6$)$_2$ instead of trans-[Tc(OH)O(DMPE)$_2$](PF$_6$)$_2$. After keeping the blue solution in a refrigerator for one day, the resultant crystals of trans-[Tc(SCH$_3$)$_2$(DEPE)$_2$]PF$_6$ were collected by filtration. Yield: 50 mg; 48%. The crystals used for x-ray analysis were obtained by slow evaporation from an ethanol solution at room temperature.

Exemplary compositions which can be made by either of the above methods include:

| 99mTc-compound | Reduction Potential |
|---|---|
| trans-[Tc(SCH$_3$)$_2$(dmpe)$_2$]$^{+/0}$ | −0.550 |
| trans-[Tc(SCH$_3$)$_2$(depe)$_2$]$^{+/0}$ | |
| trans-[Tc(SCF$_3$)$_2$(diars)$_2$]$^{+/0}$ | |
| trans-[Tc(SCH$_3$)$_2$(diars)$_2$]$^{+/0}$ | |
| trans-[Tc(SEt)$_2$(dmpe)$_2$]$^{+/0}$ | −0.566 |
| trans-[Tc(SPr)$_2$(dmpe)$_2$]$^{+/0}$ | −0.622 |
| trans-[Tc(SBz)$_2$(dmpe)$_2$]$^{+/0}$ | −0.513 |
| trans-[Tc(SCH$_2$C$_6$H$_4$OCH$_3$)$_2$(dmpe)$_2$]$^{+/0}$ | −0.559 |
| trans-[Tc(SC$_6$H$_4$Cl)$_2$(dmpe)$_2$]$^{+/0}$ | |
| cis-[Tc(SC$_6$H$_4$Cl)$_2$(dmpe)$_2$]$^{+/0}$ | |
| cis-[Tc(SC$_6$H$_5$)$_2$(dmpe)$_2$]$^{+/0}$ | |
| cis-[Tc(SC$_6$H$_4$CH$_3$)$_2$(dmpe)$_2$]$^{+/0}$ | |
| cis-[Tc(SC$_6$H$_4$OCH$_3$)$_2$(dmpe)$_2$]$^{+/0}$ | |
| cis-[Tc(SC$_6$H$_4$tBu)$_2$(dmpe)$_2$]$^{+/0}$ | |
| cis-[Tc(SC$_6$H$_4$Cl)$_2$(dmpe)$_2$]$^{+/0}$ | |
| trans-[Tc(SC$_6$H$_5$)$_2$(diars)$_2$]$^{+/0}$ | |
| trans-[Tc(SBz)$_2$(diars)$_2$]$^{+/0}$ | −0.362 |
| cis-[Tc(SPh)$_2$(diars)$_2$]$^{+/0}$ | |
| trans-[Tc(SPh)$_2$(diars)$_2$]$^{+/0}$ | −0.322 |
| [Tc(3,4-toluenedithiol-2H)(dmpe)$_2$]$^{+/0}$ | |
| cis-[Tc(SC$_6$H$_4$NO$_2$)$_2$(dmpe)$_2$]$^{+/0}$ | |
| trans-[Tc(SC$_6$H$_4$Cl)$_2$(diars)$_2$]$^{+/0}$ | |
| cis-[Tc(SPh)Cl(dmpe)$_2$]$^{+/0}$ | |
| [Tc(thioglucose-H)$_2$(diars)$_2$]$^{+/0}$ | |
| [Tc(thiocholesterol-H)$_2$(diars)$_2$]$^{+/0}$ | |
| [Tc(SCH$_3$)$_2$)diars)$_2$]$^{+/0}$ | −0.465 |
| [Tc(SCH$_2$C$_6$H$_4$OCH$_3$)$_2$(diars)$_2$]$^{+/0}$ | |
| [Tc(SPr)$_2$(diars)$_2$]$^{+/0}$ | |
| [Tc(SEt)$_2$(diars)$_2$]$^{+/0}$ | |
| [Tc(SCH$_2$CO$_2$Me)$_2$(diars)$_2$]$^{+/0}$ | |
| [Tc(SCH$_2$CO$_2$Et)$_2$(diars)$_2$]$^{+/0}$ | |
| [Tc(SCH$_2$CH$_2$OH)$_2$(diars)$_2$]$^{+/0}$ | |
| [Tc(diars)$_2$(SPh)$_2$]$^{+/0}$ | |
| [Tc(SBz)$_2$(dppe)$_2$]$^{+/0}$ | |
| [Tc(SPh)$_2$(dppe)$_2$]$^{+/0}$ | |
| [Tc(SC$_6$H$_4$Cl)$_2$(dppe)$_2$]$^{+/0}$ | |
| [Tc(SCH$_2$CO$_2$Me)$_2$(dppe)$_2$]$^{+/0}$ | |
| [Tc(SCH$_2$CO$_2$Et)$_2$(dppe)$_2$]$^{+/0}$ | |
| [Tc(SCH$_2$CO$_2$Et)(SCH$_2$CO$_2{}^-$)(dppe)$_2$]$^{+/0}$ | |
| [Tc(SCH$_2$CO$_2$Me)(SCH$_2$CO$_2{}^-$)(dppe)$_2$]$^{+/0}$ | |
| [Tc(SBZ)$_2$(dtpe)$_2$]$^{+/0}$ | |
| [Tc(SPh)$_2$(dtpe)$_2$]$^{+/0}$ | |

In the above Bz represent benzyl, et ethyl, me methyl, tBu tertbutyl and Ph phenyl, diars O-phenylene, bis(-dimethylarsine), DMPE 1,2-bis (dimethylphosphino) ethane, DPPE 1,2-bis(diphenylphosphino) ethane and dtpe 1,2-bis(ditoluylphosphino) ethane.

The complexes are designated Tc(III/II) but are generally obtained in the form of Tc(III) complexes which then can be reduced by the addition of a few drops of a mild reducing agent under anaerobic conditions. For example, the Tc(III) complex can be dissolved in acetonitrile and a few drops of tetrabutylammoniumborohydride or sodium methylsulfide added.

To test this, anaerobic solutions of the trans-[Tc(SCH$_3$)$_2$(D)$_2$]PF$_6$ where D equals DMPE or DEPE were dissolved in acetonitrile and a few drops of (C$_4$H$_9$)$_4$NBH$_4$ and a small amount of ethanol were added under an argon atmosphere. The previously blue solution almost immediately turned a purple color. The purple color could also be obtained by adding NaSCH$_3$ in a small amount of ethanol to the blue solution. Contact with the air caused the exposed surfaces of the purple solution to turn blue and bubbling air through the purple solution immediately causes the color change to a pale yellow-brown. When several drops of NH$_4$PF$_6$ in a small amount of water or an acid such as CF$_3$SO$_3$H, HPF$_6$ or HClO$_4$ were added to the purple solution under an argon atmosphere, the color reverted back to the original blue. No color change occurred when water alone was added to the purple solution. The conversion between blue and purple solution is reversible for at least four times. In these solutions the purple complex is attributed to the Tc(II) complex Tc(SCH$_3$)$_2$D$_2{}^0$. The deep blue solution is attributed to the Tc(III) complex.

To determine the reduction potential of the complexes according to the present invention, electrochemical studies were performed in 0.5 mol TEAP/DMF at a Pt disc electrode. A summary of these potential measurements is found in Table 1.

The methanethiolato technetium complexes are characterized by two reversible redox couples corresponding to the reactions [Tc$^{III}$(SCH$_3$)$_2$D$_2$]$^+$ +e$^-$ ⇌ [Tc$^{II}$(SCH$_3$)$_2$D$_2$] and [Tc$^{II}$(SCH$_3$)$_2$D$_2$]+e$^{31}$ ⇌ (Tc$^I$(SCH$_3$)$_2$D$_2$)$^-$. Electrochemical reversibility of this Tc(III)/(II) couple is established from the observations that the peak current is proportional to the square root of the scan rate, the ratio of anodic to cathodic peak occurrence is nearly unity and the separation between related cathodic and anodic peaks is close to the Nernstian value of 59 mV for a one equivalent redox process. The observed peak separations are 60 mV and 59 mV for D equals DMPE and DEPE respectively for Tc(III-/II) reaction which occurs at about −0.55V vs Ag-/AgCl (3 M NaCl). The difference in reduction potentials resulting from the differing phosphine substituents of these complexes is slight for this reaction. E$^0$ is only 4 mV more negative for the DEPE complex than the DMPE complex. The effect is more profound for the Tc(II/I) reaction were the difference is 90 mV.

The potential at which the central Tc atom undergoes reduction is an inherent component of the energy of the ligand to Tc charged transfer transition (E$_{LTMCT}$). For a series of closely related complexes a linear correlation between reduction potential and E$_{LTMCT}$ can be anticipated. The easier a complex is to reduce the lower will be E$_{LTMCT}$. Such linear corelationships have been observed.

TABLE 1

Analytical Characterizations of trans-[Tc(SCH$_3$)$_2$D$_2$)]$^+$ Complexes with D = DMPE and DEPE.

| Elemental Analyses | C % | H % | F % | P % | S % |
|---|---|---|---|---|---|

TABLE 1-continued

Analytical Characterizations of trans-[Tc(SCH$_3$)$_2$D$_2$)]$^+$ Complexes with D = DMPE and DEPE.

| | | | | | | |
|---|---|---|---|---|---|---|
| [Tc(SCH$_3$)$_2$(DMPE)$_2$]PF$_6$ | calcd. | 26.34 | 6.00 | 17.86 | 24.26 | 10.04 |
| | found | 26.36 | 5.86 | 16.75 | 23.40 | 10.74 |
| [Tc(SCH$_3$)$_2$(DEPE)$_2$]PF$_6$ | calcd. | 35.20 | 7.25 | 15.18 | 20.63 | 8.54 |
| | found | 35.29 | 7.20 | 14.89 | 20.68 | 8.36 |

| Mass Spectral Data | Complex Ion, M$^+$ | Fragment Ion, M-( ) | | | | |
|---|---|---|---|---|---|---|
| | | (CH$_3$) | (2CH$_3$) | (SCH$_3$) | (CH$_3$,SCH$_3$) | (D) | (D,2CH$_3$) |
| [Tc(SCH$_3$)$_2$(DMPE)$_2$]$^+$ | 493[1] | 478 | 463 | 446 | 430 | | |
| [Tc(SCH$_3$)$_2$(DEPE)$_2$]$^+$ | 605 | | | 558 | | 399 | 369 |

Visible-UV Spectral Data[2] (max)/10$^3$cm$^{-1}$ (E/10$^3$M$^{-1}$cm$^{-1}$)

[Tc(SCH$_3$)$_2$(DMPE)$_2$]$^+$ 16.81(12.96),28.49(1.97),29.68(4.85),46.08(11.64)
[Tc(SCH$_3$)$_2$(DEPE)$_2$]$^+$ 16.61(12.43),28.33(1.81),38.61(8.09),46.08sh(19.71)

| Electrochemical Data[3] | Tc(III/II),E$^{o'}$ | Tc(II/I),E$^{o'}$ | oxidation,E$_{pc}$[4] |
|---|---|---|---|
| [Tc(SCH$_3$)$_2$(DMPE)$_2$]$^+$ | −.559 | −1.72 | +0.925 |
| [Tc(SCH$_3$)$_2$(DEPE)$_2$]$^+$ | −.554 | −1.81 | +0.954[5] |

[1]Intense peak.
[2]In acetonitrile sh denotes a shoulder.
[3]At 25° C. in 0.5 M TEAP/DMF at PDE and scan rate = 100 mV/s. E$^{o'}$ = (E$_{pc}$ + E$_{pa}$)/2 in V vs. Ag/AgCl (3 M NaCl) from cyclic voltammetry.
[4]Irreversible at 25° C.
[5]Becomes reversible at −70° C.; see text.

Method of Use

The composition of the present invention was tested for imaging the brains of rats and guinea pigs. The various sodium borohydride reducing $^{99m}$Tc(II) agents were screened for their ability to cross the BBB in anesthetized (Metofane), female Sprague-Dawley rats of ca 200g weight. Approximately 1 mCi of $^{99m}$Tc activity per 200 g body weight was injected into the jugular vein. The complexes injected were $^{99m}$Tc(II)(-diars)$_2$(SCH$_2$C$_6$H$_5$)$_2$, $^{99m}$Tc(II)(diars)$_2$(SCH$_2$COOCH$_3$)$_2$ and $^{99m}$Tc(II)(diars)$_2$(thiocholesterol)$_2$. After intrajugular injection of the agent, the rats were sacrificed by cervical dislocation, blood samples were collected, and the brains were excised. Tissue samples were weighed (average brain weight=1.5 g) and assayed for $^{99m}$Tc by standard techniques. Analysis indicated passage of the complex through the BBB into the brain and retention at periods of from 30 seconds to 30 minutes or more with peak concentration between 30 seconds and one minute. To image the rat brain, 1 mCi/per about 200g body weight of the above $^{99m}$Tc(II) complexes are injected in the jugular vein and the brain is imaged using a tomographic scintillation camera.

The Tc(II) complexes of the present invention cross the blood-brain diffusion barrier. These compounds should remain in the brain for a period of time sufficient to permit tomographic analysis of blood flow to the brain. This provides a useful method of imaging the brain which can be practiced in virtually any radiopharmacy.

Further, these complexes, regardless of their reduction potential, may be used as blood pool imaging agents as well as kidney and liver imaging agents by well known methods.

This has been a general description of this invention as well as the best mode of practicing this invention. However, the invention is defined by the following claims, wherein:

We claim:

1. A composition of mater having the following general formula ($^{99m}$TcL$_1$L$_2$L$_3$L$_4$L$_5$L$_6$)X$_z$ wherein X is a parentally acceptable anion and X is 0 or 1

L$_1$-L$_4$ represent neutral ligands bonded to said Tc center by an atom selected from the group consisting of N, P and As and mixtures thereof and L$_5$ and L$_6$ represent anionic ligands said ligands selected from the group consisting of sulfur group containing ligands and selenium group containing ligands wherein L$_5$ and L$_6$ are bonded to said Tc by either said sulfur group or said selenium group wherein L$_1$-L$_4$ have the following formula (F$_i$)$_3$-A, wherein A represents the same or different atoms selected from the group consisting of P, As, and N; and i represents an integer from 1-4; and L$_5$ and L$_6$ have the following general formula R$_n$-Y wherein Y represents S or Se and wherein n represents an integer 5 or 6 and R$_1$, R$_2$, R$_3$, R$_4$ represent the same or different radical selected from the group consisting of hydrogen, C$_1$-C$_{20}$ alkyl, oxy alkyl (C$_1$-C$_{10}$), C$_3$-C$_{10}$ cyclo alkyl and aryl, and R$_4$ and R$_5$ represent the same or different radical selected from the group consisting of hydrogen, C$_1$-C$_{20}$ alkyl, C$_3$-C$_{10}$ cyclo alkyl, carbonyl, sulfonyl, aryl, and alkylene aryl.

2. The composition claimed in claim 1 wherein Y represents S.

3. The composition claimed in claim 1 wherein Y represents Se.

4. The composition claimed in claim 1 wherein two of said L$_1$, L$_2$, L$_3$, L$_4$ combined represent neutral ligands selected from the group consisting of DMPE, DEPE, DIARS, DIEN, DPPE AND DTPE.

5. The agent claimed in claim 7 wherein Y represents Se.

6. The agent claimed in claim 7 wherein two of said R$_1$, R$_2$, R$_3$, R$_4$ combined represent neutral ligands selected from the group consisting of DMPE, DEPE, DIARS, DIEN, DPPE and DTPE.

7. A brain perfusion imaging agent comprising a ligated Tc-99m complex wherein (1) said Tc is Tc(II);

(2) and said complex has a reduction potential Tc(III) to Tc(II), said reduction potential being
   (a) at least low enough to be oxidized to Tc(III) in vivo after crossing the blood brain diffusion barrier;
   (b) high enough to allow it to remain unoxidized to Tc(III) while in human blood for about 2 second and wherein said reduction potential is less than about +0.6 volts vs Ag/AgCl (3 M NaCl wherein said complex has the following formula $(Tc(II)L_1L_2L_3L_4L_5L_6)^0$ wherein $L_1$-$L_4$ represent neutral ligands having the following formula $(R_i)_3$-A, wherein A represents the same or different atoms selected from the group consisting of P, As, and N; and i represents an integer from 1-4; and Lhd 5 and $L_6$ represent anionic ligands having the following general formula $R_n$-Y wherein Y represents S or Se and wherein n represents an integer 5 or 6 and $R_1$, $R_2$, $R_3$, $R_4$ represent the same or different radical selected from the group consisting of hydrogen, $C_1$-$C_{20}$ alkyl, oxy alkyl ($C_1$-$C_{10}$), $C_3$-$C_{10}$ cyclo alkyl and aryl, and $R_4$ and $R_5$ the same or different radical selected from the group consisting of hydrogen, $C_1$-$C_{20}$ alkyl, $C_3$-$C_{10}$ cyclo alkyl, carbonyl, sulfonyl, aryl, and alkylene aryl.

8. The agent claimed in claim 7 wherein Y represents S.

9. The complex claimed in claim 8 wherein $R_n$-Y represents a ligand selected from the group consisting of methyl thiolate, benzyl thiolate, and 4 halo benzyl thiolate.

10. A method of imaging the brain comprising injecting an effective amount of a brain perfusion imaging agent comprising a ligated Tc-99m complex wherein said Tc is Tc(II) and;
   said complex having a reduction potential of Tc(III) to Tc(II) said reduction potential being at least low enough to be oxidized in vivo after crossing the blood brain diffusion barrier and high enough to remain unoxidized in human blood during transfer from a course of injection to said blood brain diffusion barrier and wherein said complex has a reduction potential Tc(III) to Tc(II) of less than about +0.6 volts vs Ag/AgCl (3 M NaCl) and wherein said complex has the following general formula $(Tc(II)L_1L_2L_3L_4L_5L_6)^0$ wherein $L_1$-$L_4$ represent neutral ligands having the following formula $(R_i)_3$-A wherein A represents the same or different atoms selected from the group consisting of P, As, and N; and i represents an integer from 1-4; and $L_5$ and $L_6$ represent neutral ligands having the following general formula $R_n$-Y wherein Y represents S or Se and wherein n represents an integer 5 or 6 and $R_1$, $R_2$, $R_3$ $R_4$ represent the same or different radicals selected from the group consisting of hydrogen, $C_1$-$C_{20}$ alkyl, oxy alkyl ($C_1$-$C_{10}$) cyclo alkyl and aryl, and $R_4$ and $R_5$ the same or different radical selected from the group consisting of hydrogen, $C_1$-$C_{20}$ alkyl, $C_3$-$C_{10}$ cyclo alkyl, carbonyl, sulfonyl aryl alkylene, aryl and alkylene aryl.

11. The method claimed in claim 10 wherein said complex is selected from the group consisting of $$\text{trans-}(Tc(SCF_3)_2(\text{diars})_2)^{+/0}$$

$$\text{trans-}(Tc(SBz)_2(\text{diars})_2)^{+/0}$$

$$\text{trans-}(Tc(SPh)_2(\text{diars})_2)^{+/0}$$

wherein said Tc is $^{99m}$Tc.

12. The method claimed in claim 10 wherein Y represents S.

13. The method claimed in claim 12 wherein $(R_i)_3$-A represents ligands selected from the group consisting of DMPE, DEPE, DIARS, DIEN, TRIEN, DPPE and DTPE.

* * * * *